United States Patent [19]

Ferris

[11] Patent Number: 4,588,749
[45] Date of Patent: May 13, 1986

[54] ARYLETHANOLAMINE DERIVATIVES, THEIR PREPARATION AND USE IN PHARMACEUTICAL COMPOSITIONS

[75] Inventor: Michael J. Ferris, Sutton, England
[73] Assignee: Beecham Group p.l.c., England
[21] Appl. No.: 606,597
[22] Filed: May 3, 1984

Related U.S. Application Data

[63] Continuation of Ser. No. 257,480, Apr. 23, 1981, abandoned.

[30] Foreign Application Priority Data

May 8, 1980 [GB] United Kingdom ............... 8015297

[51] Int. Cl.[4] ................... A61K 31/135; C07C 91/02
[52] U.S. Cl. .................................. 514/649; 564/347; 564/363
[58] Field of Search .............. 564/363; 424/330; 514/649

[56] References Cited

FOREIGN PATENT DOCUMENTS

| | | |
|---|---|---|
| 212209 | 4/1956 | Australia . |
| 6735 | 1/1980 | European Pat. Off. |
| 7204 | 1/1980 | European Pat. Off. |
| 21636 | 1/1981 | European Pat. Off. |
| 2135678 | 7/1971 | Fed. Rep. of Germany . |
| 5382733 | 7/1978 | Japan . |

Primary Examiner—Nicky Chan
Attorney, Agent, or Firm—Jacobs & Jacobs

[57] ABSTRACT

Compounds of formula (II):

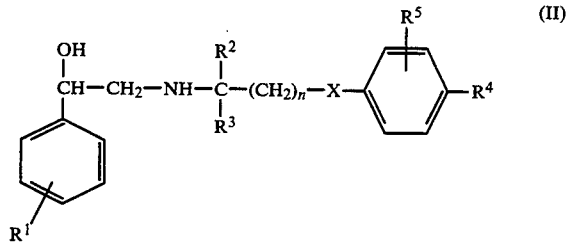

or a pharmaceutically acceptable salt thereof, in which X is an oxygen atom or a bond, $R^1$ is a hydrogen, fluorine, chlorine or bromine atom or a trifluoromethyl or $C_{1-4}$ alkyl group, each of $R^2$ and $R^3$ is a hydrogen atom or a $C_{1-4}$ alkyl group, $R^4$ is a $C_{1-4}$ alkyl group, $R^5$ is a hydrogen atom or a $C_{1-4}$ alkyl group, and n is an integer of from 1 to 3; are useful as anti-obesity and/or anti-hyperglycaemic agents.

12 Claims, No Drawings

ARYLETHANOLAMINE DERIVATIVES, THEIR PREPARATION AND USE IN PHARMACEUTICAL COMPOSITIONS

CROSS-REFERENCE

This is a continuation of Ser. No. 257,480 filed Apr. 23, 1981, now abandoned.

The present invention relates to a group of arylethanolamine derivatives which have anti-obesity and/or hypoglycaemic activity, to processes for their preparation and to their use in medicine.

European Patent Application No. 79 301197.4 discloses compounds of formula (I):

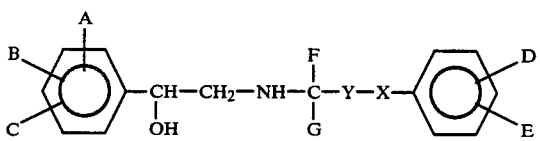

wherein
- A is hydrogen, fluorine, chlorine, hydroxyl, hydroxymethyl, methyl, methoxy, amino, formamido, acetamido, methylsulphonamido, nitro, benzyloxy, methylsulphonylmethyl, ureido, trifluoromethyl or p-methoxybenzylamino;
- B is hydrogen, fluorine, chlorine or hydroxyl;
- C is hydrogen, fluorine, chlorine or hydroxyl;
- D is a carboxylic acid group or a salt, ester or amide thereof;
- E is hydrogen, fluorine, chlorine, methyl, methoxy, hydroxyl or a carboxylic acid group or a salt, ester or amide thereof;
- F is hydrogen, methyl, ethyl or propyl;
- G is hydrogen, methyl, ethyl or propyl;
- X is oxygen or a bond; and
- Y is $C_{1-6}$ alkylene or a bond, which possess anti-obesity and/or hypoglycaemic activity.

It has now been discovered that a class of novel arylethanolamine derivatives have anti-obesity and/or hypoglycaemic activity. This activity is coupled with low cardiac stimulant activity. Derivatives of this invention also have topical anti-inflammatory activity.

According to the present invention there is provided a compound of formula (II):

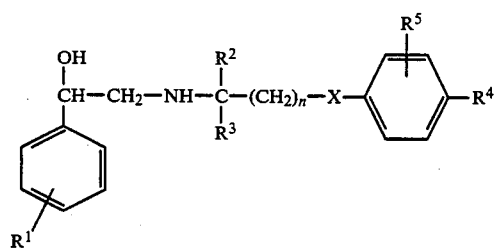

or a pharmaceutically acceptable salt thereof, in which X is an oxygen atom or a bond, $R^1$ is a hydrogen, fluorine, chlorine or bromine atom or a trifluoromethyl or $C_{1-4}$ alkyl group and is preferably in the meta position in the phenyl ring, each of $R^2$ and $R^3$ is a hydrogen atom or a $C_1$ to $C_4$ alkyl group, preferably a methyl group, $R^4$ is a $C_1$ to $C_4$ alkyl group, preferably methyl, $R^5$ is a hydrogen atom or a $C_{1-4}$ alkyl group, preferably methyl, and n is an integer of from 1 to 3.

Preferably, $R^2$ is a hydrogen atom and $R^3$ is a methyl group. Preferably $R^1$ is in the meta-position on the aromatic ring.

Preferably, n is 1 or 2, most preferably 1.

Particularly suitable compounds of this invention include those of the formula (III):

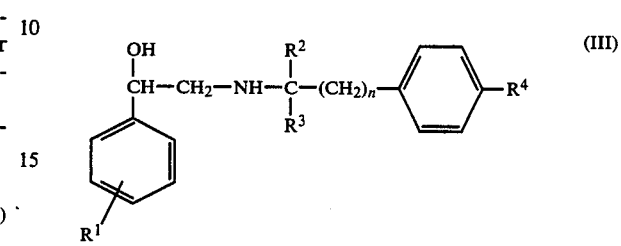

in which $R^1$ is a hydrogen, fluorine, chlorine or bromine atom or a trifluoromethyl group and $R^2$, $R^3$, $R^4$ and n are as defined in relation to formula (II).

The compounds of this invention may be provided as acid addition salts. Suitable acid addition salts include those formed with acids such as hydrochloric, hydrobromic, orthophosphoric, sulphuric, methanesulphonic, toluenesulphonic, acetic, propionic, lactic, citric, fumaric, malic, succinic, salycylic or acetylsalycylic acid.

The compounds of formula (II) have a centre of asymmetry at the carbon atom marked with a single asterisk in formula (IIa):

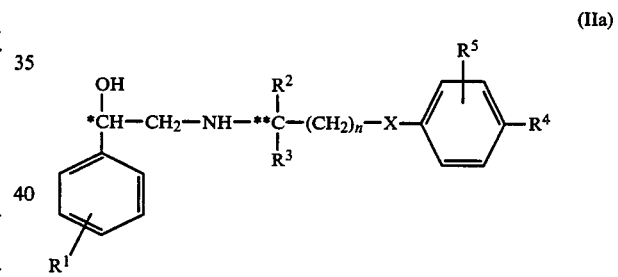

in which $R^1$, $R^2$, $R^3$, $R^4$, $R^5$, X and n are as defined in relation to formula (II). The compounds have another centre of asymmetry at the carbon atom marked with two asterisks in formula (IIa) when $R^2$ is different from $R^3$.

The compounds may, therefore, exist in at least two and often four stereoisometric forms. The present invention encompasses all stereoisomers of the compounds of formula (II) whether free from other stereoisomers or admixed with other stereoisomers in any proportion and thus includes, for instance, racemic mixtures of enantiomers.

Preferably both the *C and **C atoms have the R absolute stereochemical configuration, or the *C atom has the R configuration and the **C atom has the S configuration.

The absolute configuration of any compound of formula (II) may be determined by conventional X-ray cystallographic techniques.

It is believed that, in the $^{13}C$ n.m.r. of compounds of formula (II) wherein one of $R^2$ and $R^3$ is hydrogen and the other is methyl, the diastereoisomer having the greater anti-obesity activity is that for which the signal of the methyl group carbon atom α to the nitrogen atom appears at higher field (the lower numerical value when expressed in ppm) in $d_6$DMSO solution. The paired resonances often appear at approximately 20 ppm (less active) and slightly below 20 ppm (more active) down field from tetramethylsilane. Other paired resonances can occur for the carbon atoms attached directly to the nitrogen atom and the carbon which carries the hydroxyl and phenyl groups. Again the paired resonances of the more active diastereoisomer of the investigated compounds appear at the higher field position.

The present invention also provides a process for producing a compound of formula (II) or a salt thereof, which process comprises reducing an oxo-group and/or a double bond and/or an ester group of a compound of formula (IV):

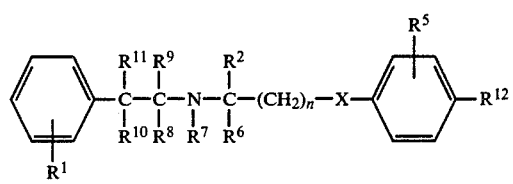
(IV)

wherein $R^1$, $R^2$, $R^5$, X and n are as defined in relation to formula (II), $R^{12}$ is a group $R^4$ as defined in relation to formula (II), or a group

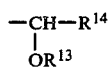

wherein $R^{13}$ is a hydrogen atom or an ester forming group and $R^{14}$ is a hydrogen atom or a $C_{1-3}$ alkyl group;

$R^6$ is a group $R^2$ as defined in relation to formula (II) or together with $R^7$ forms a bond;

$R^7$ is hydrogen or together with $R^6$ or $R^8$ forms a bond;

$R^8$ is hydrogen or together with $R^9$ forms an oxo-group or together with $R^7$ forms a bond;

$R^9$ is hydrogen or together with $R^8$ forms an oxo-group;

$R^{10}$ is hydrogen or hydroxyl or together with $R^{11}$ forms an oxo-group;

$R^{11}$ is hydrogen or together with $R^{10}$ forms an oxo-group, provided that there is no more than one oxo-group and no more than one bond represented by any of $R^6$ to $R^{11}$, and optionally thereafter forming a salt of the compound of formula (II) so formed.

The aforementioned reductions may be effected by conventional chemical or catalytic methods, such as chemical reduction using lithium aluminium hydride, sodium cyanoborohydride or sodium borohydride or by catalytic hydrogenation using catalysts such as palladium on charcoal, or platinum, for instance, as platinum oxide.

Reduction by sodium borohydride is conveniently effected in a lower alkanolic solvent such as methanol. The reaction is generally carried out at from 0°–20° C.

Reduction by lithium aluminium hydride is conveniently effected in a dry, ether solvent such as diethyl ether or tetrahydrofuran at ambient or elevated temperature.

Catalytic reduction is conveniently effected in a conventional hydrogenation solvent such as a lower alkanol, for instance ethanol. The hydrogenation is gener-ally carried out under hydrogen gas at about 1 atmosphere pressure to about 10 atmospheres pressure and at ambient or elevated temperature.

In particular process aspects, the present invention provides processes for producing compounds of formula (II) by reducing a compound of formula (IVA):

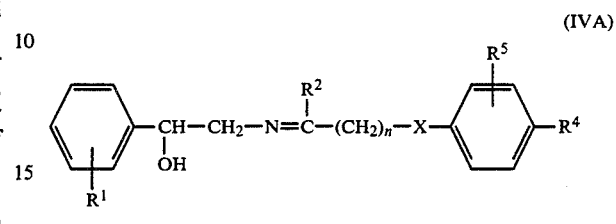

or reducing a compound of formula (IVB):

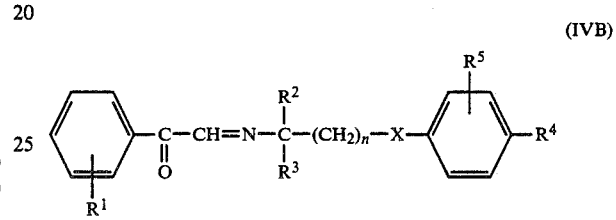

or reducing a compound of formula (IVC):

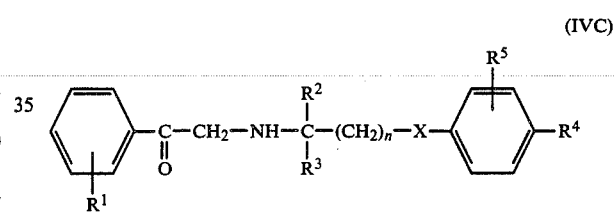

or reducing a compound of formula (IVD):

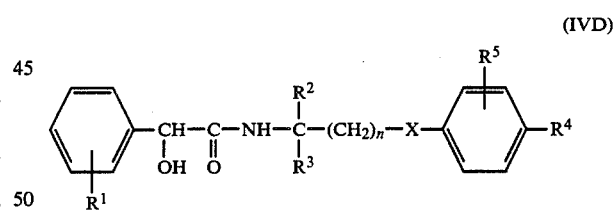

or reducing a compound of formula (IVE):

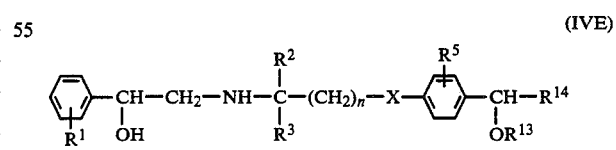

wherein $R^1$, $R^2$, $R^3$, $R^4$, $R^5$, X and n are as defined in relation to formula (II) and $R^{13}$ and $R^{14}$ are as defined in relation to formula (IV).

The present invention also provides another process for producing a compound of formula (II) or a salt thereof, which process comprises reacting a compound of formula (V):

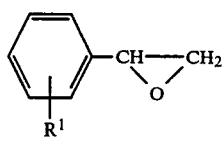

with a compound of formula (VI):

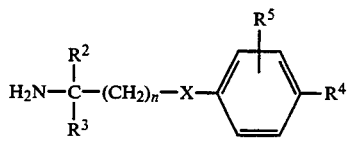

wherein $R^1$, $R^2$, $R^3$, $R^4$, $R^5$, X and n are as defined in relation to formula (II), and optionally thereafter forming a salt of the compound of formula (II) so formed.

This reaction is conveniently effected in a solvent such as a lower alkanol, preferably ethanol.

A particularly preferred process for producing compounds of formula (II) comprises the reduction of a compound of formula (IVA), especially using sodium borohydride in methanol at ambient temperature.

The salts of compounds of formula (II) may be produced by treating the compound of formula (II) with the appropriate acid.

Compounds of formula (II) and salts thereof, produced by the above processes, may be recovered by conventional methods.

Compounds of formula (II) having a single asymmetric carbon atom may, if desired, be separated into individual enantiomers by conventional means, for example, by the use of an optically active acid as a resolving agent. Those compounds of formula (II) having two asymmtric carbon atoms may be separated into diastereoisomeric pairs of enantiomers by, for example, fractional crystallisation from a suitable solvent such as ethyl acetate. The pair of enantiomers thus obtained may be separated into individual stereoisiomers by conventional means such as by the use of an optically active acid as a resolving agent.

Suitable optically active acids which may be used as resolving agents are described in "Topics in Stereochemistry" Vol 6, Wiley Interscience, 1971, Allinger, N. L. and Eliel, W. L. Eds.

Alternatively any enantiomer of a compound of formula (II) may be obtained by stereospecific synthesis using an optically pure starting material of known configuration.

Compounds of formula (IV) may be produced by reacting a compound of formula (VII):

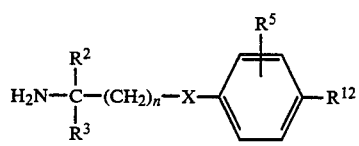

wherein $R^2$, $R^3$, $R^5$, X and n are as defined in relation to formula (II), and $R^{12}$ is as defined in relation to formula (IV), with a compound of formula (VIII):

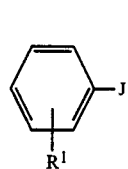

wherein $R^1$ is as defined in relation to formula (II) and J is a reactive moiety which is capable of reacting with the amine of formula (VII) thus forming a compound of formula (IV). Typical examples of compounds of formula (VIII) are:

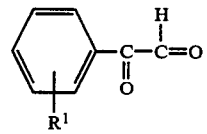

or its hydrate or hemi-acetal of a lower alkanol;

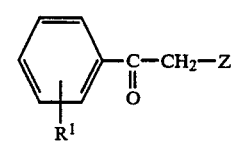

wherein Z is a halogen atom, preferably bromine

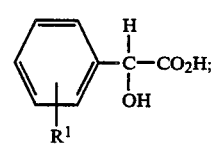

and

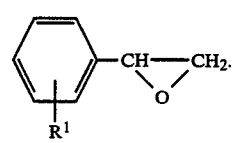

Conventional conditions suitable for use with the particular compound of formula (VIII) may be used for this reaction. Thus the reaction of a compound of formula (VIIIA) with a compound of formula (VII) is conveniently conducted at elevated temperature under conditions resulting in the removal of the water formed during the reaction. A particularly suitable method is to perform the reaction in a solvent, such as benzene, under reflux and azeotropically to remove the water using a Dean & Stark trap.

The reaction of a compound of formula (VIIIB) with a compound of formula (VII) is conveniently conducted in a polar organic solvent such as acetonitrile or butanone, at an elevated temperature, for instance under reflux.

The reaction of a compound of formula (VIIIC) with a compound of formula (VII) is conveniently conducted under standard peptide formation reaction conditions.

The reaction of a compound of formula (VIIID) with a compound of formula (VII) is conveniently conducted in a solvent such as a lower alkanol, preferably ethanol.

By using single enantiomers of a compound of formula (VII) and a compound of formula (VIII) such as the compounds (VIIIC) or (VIIID) a stereospecific synthesis of a compound of formula (IV) is achieved. This may then be reduced to a compound of formula (II) without altering the configuration of the two asymmetric carbon atoms. Thus, for example, a compound of formula (VII) with the R absolute configuration and a compound of formula (VIIID) with the R absolute configuration would afford a compound of formula (II) with the RR absolute configuration.

Certain compounds of formula (IV) may also be produced by reacting a compound of formula (IX):

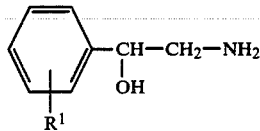

(IX)

with a compound of the formula (X):

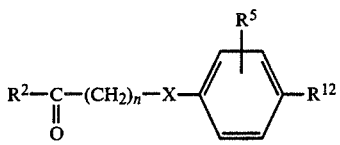

(X)

wherein $R^1$, $R^2$, $R^5$, X and n are as defined in relation to formula (II), and $R^{12}$ is as defined in relation to formula (IV).

This reaction is conveniently effected under conditions which result in the removal of water formed during the reaction. A particularly suitable method is to perform the reaction in a solvent, such as benzene, under reflux and azeotropically to remove the water using a Dean & Stark trap.

It is often convenient to prepare the compound of formula (IV) and reduce it, in situ, to the desired compound of formula (II) without isolation of the compound of formula (IV).

A compound of formula (II) or a pharmaceutically acceptable salt thereof (hereinafter "the drug") may be administered as the pure drug, however, it is preferred that the drug be administered as a pharmaceutical composition also comprising a pharmaceutically acceptable carrier.

Accordingly, the present invention also provides a pharmaceutical composition comprising a compound of the formula (II) or a pharmaceutically acceptable salt thereof with a pharmaceutically acceptable carrier therefor.

As used herein the terms "pharmaceutical composition" and "pharmaceutically acceptable" embrace compositions and ingredients for both human and veterinary use.

Usually the compositions of the present invention will be adapted for oral administration although compositions for administration by other routes, such as by injection, are also envisaged.

Particularly suitable compositions for oral administration are unit dosage forms, such as tablets and capsules. Other fixed-unit dosage forms, such as powders presented in sachets, may also be used.

In accordance with conventional pharmaceutical practice the carrier may comprise a diluent, binder, filler, disintegrant, wetting agent, lubricant, colourant, flavourant, or the like.

Typical carriers may, therefore, comprise such agents as microcrystalline cellulose, starch, sodium starch glycollate, polyvinylpyrrolidone, polyvinylpolypyrrolidone, magnesium stearate, sodium lauryl sulphate, sucrose, and the like.

Most suitable the composition will be provided in unit dose form. Such unit doses will normally comprise 0.1 to 500 mg of the drug, more usually 0.1 to 250 mg and favourably 0.1 to 100 mg.

The present invention further provides a method for treating obesity in human or non-human animals, which method comprises administering an effective, non-toxic amount of a compound of formula (II) or a pharmaceutically acceptable salt thereof to the obese animals.

In treating obese humans, the drug may be taken in doses, such as those described above, one to six time a day in a manner such that the total daily dose for a 70 kg adult will generally be about 0.1 to 1000 mg, and more usually about 1 to 500 mg.

In treating obese non-human animals, especially dogs, the drug may be administered by mouth, usually once or twice a day and at about 0.025 to 2.5 mg/kg, for example 0.1 to 2 mg/kg.

The present invention further provides a method for treating hyperglycaemia in humans which method comprises administering an effective, non-toxic amount of a compound of formula (II) or a pharmaceutically acceptable salt thereof to hyperglycaemic humans.

The drug may be taken in doses such as those described above for treating obese humans.

The present invention further provides a method for treating inflammation in human and non-human animals, which method comprises administering an effective, non-toxic amount of a compound of formula (II) or a pharmaceutically acceptable salt thereof to the animals.

The drug may be taken in doses such as those described above for treating obese animals.

The invention will now be illustrated with reference to the following Examples, which are not intended to limit the scope in any way.

EXAMPLE 1

N-[2-(4-Methylphenyl)-1-methylethyl]-2-hydroxy-2-(3-chlorophenyl)ethanamine

A mixture of 4-methylphenylacetone (1.56 g) and 2-(3-chlorophenyl)-2-hydroxyethanamine (1.81 g) was refluxed in benzene (70 ml) under Dean & Stark conditions for 4 h. The solvent was removed under reduced pressure, replaced with ethanol (100 ml) and the solution hydrogenated using Pt as catalyst. The filtered solution was evaported and the residual oil chromatographed on Kieselgel 60 (150 g). Elution with 1% methanol-chloroform gave the title compound (1.8 g) as an oil. Crystallisation from hexane gave 1.26 g as a 56:44 mixture of diastereoisomers, mp 76–78.

τ (CDCl₃) 8.95 (3H, d), 7.73 (3H, s), 6.94–7.64 (7H, m, 2H, disappears on D₂O), 5.5 (1H, m), 2.65–2.35 (8H, m).

Repetition of the above experiment and recrystallisation of the chromatographed material twice from ethyl acetate gave (1R, 2'S; 1S, 2'R)-N-(2-(4-methylphenyl)-1-methylethyl)-2'-hydroxy-2'-(3-chlorophenyl)ethanamine as white crystals, mp 106–109 (2:98 mixture of diastereoisomers).

EXAMPLE 2

N-[2-(4-Isopropylphenyl)-1-methylethyl]-2-hydroxy-2-phenylethanamine

A mixture of 4-isopropylphenylacetone (2.64 g) and 2-hydroxy-2-phenylethanamine (2.05 g) were refluxed in benzene (70 ml) under Dean & Stark conditions for 4 h. The solvent was removed under reduced pressure, replaced with ethanol (100 ml) and the solution hydrogenated using Pt as catalyst. The filtered solution was evaporated and the residual oil chromatographed on Kieselgel 60 (150 g). Elution with 2% methanol-chloroform gave the title compound as an oil (3.92 g). Treatment of this with a methanolic solution of fumaric acid and recrystallisation of the solid from ethylacetate gave the title compound (58:42 mixture of diastereoisomers) as the hemi fumarate containing one mole of water, mp 55–57.

$\tau$ (DMSO) 8.86 (3H, d), 8.84 (6H, d), 6.3–7.5 (6H, m), 5.0 (1H, m), 3.4 (2H, s), 2.82 (4H, s), 2.63 (5H, m), 0.2 (4H, broad s, disappears with $D_2O$).

EXAMPLE 3

N-[2-(4-Methylphenyl)-1-methylethyl]-2-hydroxy-2-phenyl ethanamine

A mixture of 4-methylphenylacetone (2.7 g) and 2-hydroxy-2-phenylethanamine (2.5 g) was refluxed in benzene (70 ml) under Dean & Stark conditions for 4h. The solvent was removed under reduced pressure, replaced with methanol (100 ml) and cooled in ice during the portionwise addition of sodium borohydride (3.0 g). The solution was stirred for 2 h, the solvent was evaporated under reduced pressure and the residue was partitioned between water (100 ml) and chloroform (100 ml). The organic extract was dried ($MgSO_4$), the solvent was evaporated and the residual oil was crystallised from hexane to give the title compound (2.1 g) as a 44:56 mixture of diastereoisomers, mp 74°–94°.

$\tau$ (CDCl$_3$): 8.99 (3H, d), 7.70 (3H, s), 7.0–7.6 (7H, m), 5.4 (1H, m), 3.6–4.1 (9H, m).

Repetition of the above experiment, chromatography on silica gel 60 in 2% methanol/chloroform and crystallisation of the product from methanol gave 1R,2'S; 1S,2'R-N-[2-(4-methylphenyl)-1-methylethyl]-2'-hydroxy-2'-phenyl ethanamine as colourless crystals, mp 98°–103° (2:98 ratio of diastereoisomers).

EXAMPLE 4

N-[2-(4-Methylphenyl)-1-methylethyl]-2-hydroxy-2-phenyl ethanamine

A mixture of acetyl chloride (1.4 g) and 4-hydroxymethylphenyl acetone (3.0 g) in dichloromethane (100 ml) was stirred at ambient temperature for 16 h. The solvent was evaporated to give an oil, the 16 nmr spectrum of which was consistent with 4-acetyl oxymethylphenyl acetone.

$\tau$ (CDCl$_3$) 7.98 (3H, s), 7.9 (3H, s), 6.4 (2H, s), 5.0 (2H, s), 2.85 (2H, d, J=8 Hz), 2.7 (2H, d, J=8 Hz).

A mixture of this oil (3.6 g) and 2-hydroxy-2-phenyl ethanamine (2.4 g) was refluxed in benzene under Dean & Stark conditions for 4 h. The solvent was removed under reduced pressure, ethanol added and the solution hydrogenated at 75 psi and 60° for 8 h using $PtO_2$ as catalyst. Filtration of the catalyst and evaporation of the solvent gave the title compound as an oil crystallising from hexane as an 80:20 mixture of diastereoisomers, mp 100°–104°.

$\tau$ (CDCl$_3$) 8.85 (3H, d, J=6 Hz), 8.0 (3H, s), 7.68 (3H, s), 6.7–7.2 (4H, m), 5.05 (1H, t, J=6 Hz), 2.9 (4H, s), 2.85 (3H, s, disappears with $D_2O$), 2.65 (5H, m).

EXAMPLE 5

N-[2-(4-Methylphenyl)-1-methylethyl]-2-hydroxy-2-(3-trifluoromethylphenyl)ethanamine A mixture of 2-hydroxy-2-(3-trifluoromethylphenyl)ethanamine (2.05 g) and 4-methylphenylacetone (1.48 g) was refluxed in benzene (70 ml) under Dean & Stark conditions for 4h. The solvent was removed under reduced pressure, replaced with methanol and sodium borohydride (3 g) added portionwise. The solvent was evaporated under reduced pressure, the residue partitioned between water and ether and the ether layer dried ($MgSO_4$). Removal of the solvent under reduced pressure gave an oil which was dissolved in methanol and treated with an equivalent amount of methanolic fumaric acid. Evaporation of the solvent gave the title compound (fumarate salt) as a 58:42 mixture of diastereoisomers, mp 138°–144° (EtOAc).

$\tau$ (d$_6$DMSO) 8.95 (3H, d, J=6 Hz), 7.75 (3H, s), 6.6–7.2 (5H, m), 5.0 (1H, m), 3.45 (2H, s), 2.9 (4H, s), 2.2–2.5 (4H, m), 1.7 (4H, broad, disappears with $D_2O$).

EXAMPLE 6

N-[3-(4-Methylphenyl)-1-methylpropyl]-2-hydroxy-2-(3-chlorophenyl)ethanamine

A mixture of 4-(4-Methylphenyl)butan-2-one (1.62 g) and 2-(3-chlorophenyl)-2-hydroxyethanamine (1.71 g) was refluxed in benzene under Dean & Stark conditions for 4 h. The solvent was removed under reduced pressure, replaced with methanol (100 ml) and sodium borohydride (2 g) added portionwise. The solvent was evaporated under reduced pressure, the residue partitioned between water and ether and the ether layer dried ($MgSO_4$). Removal of the solvent gave an oil which was chromatographed on Kieselgel 60. Elution with 1% methanol-chloroform gave the title compound as an 11:89 mixture of diastereoisomers, mp 75–106 (hexane).

$\tau$ (CDCl$_3$) 8.95 (3H, d, J=6 Hz), 8.1–8.5 (2H, m), 7.7 (3H, s), 6.95–7.5 (5H, m), 5.4 (1H, m), 2.95 (4H, s), 2.6–2.85 (4H, m).

EXAMPLE 7

N[1-(S)-2-(4-Methylphenyl)-1-methylethyl]-2-(R)-2-hydroxy-2-phenyl ethanamine

The title compound was prepared in the manner described in Example 3, replacing 2-hydroxy-2-phenylethanamine with 2-(R)-2-hydroxy-2-phenyl ethanamine. One recrystallisation from hexane gave the title compound as a 33:67 mixture of diastereoisomers, mp 56–60. A second recrystallisation from hexane gave the title compound as a 4:96 mixture of diastereoisomers, mp 88–89.

EXAMPLE 8

N[2-(2-Methylphenyl)-1-methylethyl]-2-hydroxy-2-(2-fluorophenyl)ethanamine

A mixture of 2-hydroxy-2-(2-fluorophenyl)ethanamine (1.54 g) and 4-methylphenylacetone (1.48 g) was refluxed in benzene (70 ml) under Dean & Stark conditions for 4h. The solvent was removed under reduced pressure, replaced with methanol and sodium borohydride (3 g) added portionwise. The solvent was evaporated under reduced pressure, the residue partitioned between water and ether and the ether layer dried (MgSO$_4$). Removal of the solvent under reduced pressure gave an oil which was chromatographed on Kieselgel 60. Elution with 1% methanol-chloroform gave the title compound (1.58 g) as a 49:51 mixture of diastereoisomers, mp 65–68 (hexane).

τ (CDCl$_3$) 8.95 (3H, d, J=6 Hz), 7.7 (3H, s), 6.9–7.6 (7H, m, 2H disappears with D$_2$O), 5.15 (1H, m), 2.75–3.2 (8H, m), 2.5 (1H, m).

EXAMPLE 9

N-[2-(4-Methylphenyl)-1,1-dimethylethyl]-2-hydroxy-2-(3-trifluoromethylphenyl)ethanamine A mixture of 3-trifluoromethylphenyl glyoxal (3.1 g) and 2-(4-methylphenyl)-1,1-dimethylethanamine (2.5 g) in benzene (100 ml) was heated under Dean & Stark conditions for 4 h. The solvent was replaced with methanol (100 ml) and sodium borohydride (3.0 g) was added portionwise with ice cooling and stirring. The mixture was stirred at ambient temperature for 2 h, evaporated to dryness and the residue was partitioned between water (100 ml) and chloroform (100 ml). The chloroform extract was dried (MgSO$_4$), evaporated and the oil was chromatographed on silica gel 60. Elution with 2% methanol/chloroform gave an oil (3.0 g) which was converted to the fumarate salt, isolated from ethanol/ether, mp 163°–5° (2.4 g).

τ (DMSO d$_6$): 8.95 (6H, s), 7.7 (3H, s), 6.7–7.3 (4H, m), 5.0 (1H, m), 3.4 (1H, s), 2.9 (4H, s), 1.8–2.5 (6H, m).

EXAMPLE 10

N-[1-R-2-(4-Methylphenyl)-1-methylethyl]-2-R-2-hydroxy-2-phenyl ethanamine

A solution of R-mandelic acid (2.5 g) and 1-hydroxybenzotriazole (2.2 g) in dimethylformamide (15 ml) was added to a stirred ice-cooled solution of 1-R-2-(4-methylphenyl)-1-methylethanamine (2.4 g) in dimethylformamide (95 ml) under nitrogen. A solution of dicyclohexyecarbodiimide (3.6 g) in dimethylformamide (36 ml) was added dropwise, the mixture was stirred at 0° for 2 h and then allowed to stand at 0° for 16 h. The precipitate was filtered off and the filtrate was evaporated. The residue was dissolved in chloroform (100 ml), washed with sodium bicarbonate solution and dried (MgSO$_4$). The solvent was evaporated to give N-[1-R-2-(4-methylphenyl)-1-methylethyl]-2-R-2-hydroxy-1-oxo-2-phenylethanamine as an oil (5.1 g) which crystallised on standing.

τ (CDCl$_3$): 9.0 (3H, d, J=6 Hz), 7.75 (3H, s), 7.2–7.5 (3H, m), 5.8 (1H, m), 5.2 (1H, s), 3.7 (1H, m), 2.5–3.3 (9H, m).

The solid (5.1 g) was taken up in dry tetrahydrofuran (50 ml) and added to a stirred suspension of lithium aluminium hydride (2.0 g) in dry THF (30 ml) under nitrogen. The mixture was refluxed for 2 h and then cooled in ice during the addition of water (2 ml), 2N sodium hydroxide (2 ml), and water (6 ml). The precipitate was filtered off, washed with THF and the combined filtrate and washings was evaporated to an oil. The product was taken up in chloroform, dried (MgSO$_4$) and the solvent was evaporated, prior to chromatography on silica gel 60 in 2% methanol/chloroform. The title compound was obtained as a colourless oil which crystallised form ether, mp 82.5°–85° $[\alpha]_D^{25}$ (ethanol) −44.4° (98% enantiomeric purity).

τ (CDCl$_3$) 8.95 (3H, d, J=6 Hz), 7.7 (3H, s), 7.0–7.7 (6H, m), 5.4 (1H, m), 2.5–3.1 (9H, m).

EXAMPLE 11

N-[1-S-2-(4-Methylphenyl)-1-methylethyl]-2-R-2-hydroxy-2-(3-trifluoromethylphenyl)ethanamine N-[1-S-2-(4-methylphenyl)-1-methylethyl]-2-R-2-hydroxy-1-oxo-2-(3-trifluoromethylphenyl)ethanamine was made by the method of Example 10, replacing R-mandelic acid with R-2-hydroxy-2-(3-trifluoromethylphenyl)ethanoic acid and 1-R-2-(4-methylphenyl)-1-methylethanamine by the S-enantiomer.

τ (CDCl$_3$): 9.0 (3H, d, J=6 Hz), 7.7 (3H, s), 7.2–7.5 (3H, m), 5.8 (1H, m), 5.1 (1H, s), 3.4 (1H, m), 2.2–3.3 (8H, m).

This intermediate was reduced with lithium aluminium hydride as in Example 10 to give the title compound, isolated as the fumarate salt, mp 132°–3° $[\alpha]_D^{25}$ −12.04° (96% enantiomeric purity).

τ (DMSO d$_6$): 8.95 (3H, d, J=6 Hz), 7.7 (3H, s), 6.6–7.2 (4H, m), 5.1 (1H, m), 3.4 (1H, s), 3.15 (2H, br, s), 2.9 (4H, s), 2.1–2.6 (4H, m).

EXAMPLE 12

N-[1-R-2-(4-Methylphenyl)-1-methylethyl]-2-R-2-hydroxy-2-(3-trifluoromethylphenyl)ethanamine N-[1-R-2-(4-Methylphenyl)-1-methylethyl]-2-R-2-hydroxy-1-oxo-2-(3-trifluoromethylphenyl)ethanamine was made by the method of Example 10, replacing R-mandelic acid with R-2-hydroxy-2-(3-trifluoromethylphenyl)ethanoic acid.

τ (CDCl$_3$): as Example 11.

This intermediate was reduced with lithium aluminium hydride as in Example 10 to give the title compound, isolated as the fumarate salt, mp 120°–1°, $[\alpha]_D^{25}$ −38.75° (98% enantiomeric purity).

τ (DMSO d$_6$): as Example 11.

EXAMPLE 13

N-(2-(4-Methylphenyl)-1-methylethyl)-2-hydroxy-2-(3-bromophenyl)ethanamine

The title compound was prepared in the manner described in Example 3 replacing 2-(3-chlorophenyl)-2-hydroxyethanamine with 2-(3-bromophenyl)-2-hydroxyethanamine. Recrystallisation of the chromatographed material from hexane gave the title compound as a 34:66 mixture of diastereoisomers, mp 75°–97°.

τ (CDCl$_3$) 8.97 (3H, d, J=6 Hz), 7.7 (3H, s), 6.95–7.65 (7H, m, 2H disappears with D$_2$O), 5.5 (1H, m), 2.4–3.15 (8H, m).

EXAMPLE 14

N-(2-(4-Methylphenyl)-1-methylethyl)-2-hydroxy-2-(3-fluorophenyl)ethanamine

The title compound was prepared in the manner described in Example 3 replacing 2-(3-chlorophenyl)-2-hydroxyethanamine with 2-(3-fluorophenyl)-2-hydroxyethanamine. The chromatographed material was treated with methanolic fumaric acid and the derived salt recrystallised from ethyl acetate to give the title compound (fumarate), mp 58–83, as a 52–48 mixture of diastereoisomers.

τ (d$_6$DMSO) 8.9 (3H, d, J=6 Hz), 7.7 (3H, s), 6.6–7.6 (5H, m), 5.05 (1H, d, J=6 Hz), 3.5 (2H, s), 2.9 (4H, s), 2.45–2.9 (4H, m), 1.5 (4H, broad, disappears with D$_2$O).

EXAMPLE 15

N-(2-(4-Methylphenylethyl)-2-hydroxy-2-(3-trifluoromethylphenyl)ethanamine

The title compound was prepared in the manner described in Example 9, replacing 2-(4-methylphenyl)-1,1-dimethylethanamine by 2-(4-methylphenyl)ethanamine. The chromatographed material was treated with ethereal hydrogen chloride and the derived salt recrystallised from ethanol-ether to give the title compound (HCl salt), mp 166–170.

$\tau$ (d$_6$DMSO) 7.7 (3H, s), 6.5–7.3 (6H, m), 4.9 (1H, m), 2.65 (1H, broad, disappears with D$_2$O), 2.85 (4H, s), 2.3–2.4 (4H, m), 0.9 (2H, broad, disappears with D$_2$O).

EXAMPLE 16

N-(3-(4-Methylphenyl)propyl)-2-hydroxy-2-(3-trifluoromethylphenyl)ethanamine

The title compound was prepared in the manner described in Example 3, replacing 2-(3-chlorophenyl)-2-hydroxy ethanamine by 2-(3-trifluoromethylphenyl)-2-hydroxyethanamine, and 4-methylphenylacetone by 4-(4-methylphenyl)butan-2-one. The chromatographed material was recrystallised from hexane to give the title compound mp 52°–55° as a 44:56 ratio of diastereoisomers.

$\tau$ (d$_6$DMSO) 9.1 (3H, d, J=6 Hz), 8.25–8.75 (2H, m), 7.75 (3H, s), 7.25–7.7 (5H, m), 5.4 (1H, m), 4.5 (1H, broad, disappears with D$_2$O), 3.0 (4H, s), 2.25–2.5 (4H, m).

EXAMPLE 17

N-(3-(4-Methylphenyl)-1,1-dimethylpropyl)-2-hydroxy-2-phenyl ethanamine

The title compound was prepared in the manner described in Example 9, replacing 2-(4-methylphenyl)-1,1-dimethylethanamine by 3-(4-methylphenyl)-1,1-dimethylpropanamine and 3-trifluoromethylphenyl glyoxal by phenylglyoxal. The chromatographed material was recrystallised from hexane to give the title compound m.p. 107–110. $\tau$ (CDCl$_3$) 8.95 (6H, s), 8.2–8.7 (2H, m), 7.8 (3H, s), 7.3–7.7 (4H, m), 5.7–6.5 (2H, m), 5.5 (1H, t, J=6 Hz), 2.9 (4H, s), 2.7 (4H, m).

EXAMPLE 18

N-(3-(4-Methylphenyl)-1,1-dimethylpropyl)-2-hydroxy-2(3-trifluoromethylphenyl)ethanamine The title compound was prepared in the manner described in Example 9 replacing 2-(4-methylphenyl)-1,1-dimethylethanamine by 3-(4-methylphenyl)-1,1-dimethylpropanamine. The chromatographed material was treated with ethanolic fumaric acid and the crude solid recrystallised from ethyl acetate to give the title compound (fumarate salt) m.p. 170–172. $\tau$ (d$_6$DMSO) 8.7 (6H, s), 7.9–8.35 (2H, m) 7.7 (3H, s), 6.7–7.3 (4H, m), 4.9 (1H, m), 3.45 (2H, s), 2.9 (4H, s), 1.6–2.5 (4H, m+4H, disappears with D$_2$O)

EXAMPLE 19

N-(2-(4-Methylphenyl)ethyl)-2-hydroxy-2-phenylethanamine

The title compound was prepared in the manner described in Example 9, replacing 2-(4-methylphenyl)-1,1-dimethylethanamine by 2-(4-methylphenyl)ethanamine and 3-trifluoromethylphenylglyoxal by phenylglyoxal. The chromatographed material was recrystallised from hexane to give the title compound, mp 95°–97°.

$\tau$ (CDCl$_3$) 7.7 (3H, s), 7.0–7.5 (6H, m, +2H disappears with D$_2$O), 5.4 (1H, dd, J=6 Hz, J=6 Hz), 2.9 (4H, s), 2.7 (5H, s).

EXAMPLE 20

N-(3-(4-Methylphenyl)propyl)-2-hydroxy-2-(3-chlorophenyl)ethanamine

The title compound was prepared in the manner described in Example 9 using 3-chlorophenylglyoxal and 3-(4-methylphenyl)propanamine. Recrystallisation of the chromatographed material from ether gave the title compound, mp 115°–117.5°.

$\tau$ (CDCl$_3$) 8.4–8.0 (2H, m), 7.66 (3H, s), 7.63–7.1 (8H, m inc two exchangeable protons), 5.36 (1H, m), 3.06–2.56 (8H, m).

EXAMPLE 21

N-(2-(4-Butylphenyl)-1-methylethyl)-2-hydroxy-2-phenylethanamine

The title compound was prepared in the manner described in Example 3 using phenylglyoxal and 4-t-butylphenylacetone. Treatment of the chromatographed material with ethereal hydrogen chloride gave the salt m.p. 139–155 (ethyl acetate) isolated as a 82:18 mixture of diastereoisomers. $\tau$ (d$_6$DMSO) 8.9 (3H, d, J=6 Hz), 8.8 (9H, s), 7.4–7.0 (5H, m), 4.9 (1H, m), 3.8 (1H, disappears with D$_2$O), 2.8 (2H, d), 2.65 (2H, d), 2.5 (5H, m), 1.0–0.0 (2H, disappears with D$_2$O.)

EXAMPLE 22

N-(2(4-Methylphenyl)ethyl)-2-(R)-2-hydroxy-2-(3-trifluoromethylphenyl)ethanamine A solution of R-3-trifluoromethylstyrene oxide (1.9 g) in ethanol (10 ml) was added dropwise to a stirred solution of 4-methylphenylethanamine (1.4 g) in ethanol (50 ml). After complete addition the solution was heated under reflux for 48 hours, the ethanol evaporated and the residue chromatographed on silica gel 60 using 2% methanol in chloroform as eluent. The title compound was obtained as an oil (0.5 g), and was converted into a hydrochloride salt, and recrystallised to constant melting point 180–184 (methanolether). $(\alpha)_D^{25}$ −25.7° (ethanol). $\tau$(CDCL$_3$) 7.70 (3H, s), 6.5–7.2 (6H, m), 4.85 (1H, m), 3.58 (1H, broad, replaceable by D$_2$O), 2.86 (4H, s), 2.1–2.4 (4H, m), 0.66 (2H, broad, replaceable by D$_2$O).

EXAMPLE 23

N-(3-(4-Methylphenyl)propyl)-2-hydroxy-2-(3-trifluoromethylphenyl)ethanamine

The title compound was prepared in the manner described in Example 9 using 3-trifluoromethylphenylglyoxal and 3-(4-methylphenyl)propanamine. Recrystallization of the chromatographed material from hexane gave the title compound m.p. 96–98. $\tau$(CDCl$_3$) 8.0–8.5 (2H, m), 7.7 (3H, s), 7.0–7.5 (6H, m+2H, disappears with D$_2$O), 5.3 (1H, dd), 2.9 (4H, s), 2.3–2.7 (4H, m).

EXAMPLE 24

N-(2-(4-Methylphenyl)ethyl)-2-hydroxy-2-(3-chlorophenyl)ethanamine

The title compound was prepared in the manner described in Example 9 using 3-chlorophenylglyoxal and 2-(4-methylphenyl)ethanamine. Recrystallization of the chromatographed material from cyclohexane gave the title compound m.p. 85–88 (analysed as the hemihydrate). τ(CDCl₃) 7.7 (3H, s), 7.0–7.5 (6H, m, +2H disappears with D₂O), 5.4 (1H, dd), 2.9 (4H, s), 2.6–2.8 (4H, m).

EXAMPLE 25

N-(2-(4-Ethylphenyl)-1-methylethyl)-2-hydroxy-2-phenylethanamine

The title compound was prepared in the manner described in Example 3 using 2-hydroxy-2-phenylethanamine and 4-ethylphenyl acetone. Recrystallization of the chromatographed material from hexane gave the title compound m.p. 76–82 as a 19:81 mixture of diastereoisomers (analysed as the hemi-hydrate). τ(CDCl₃), 8.9 (3H, d, J=6 Hz), 8.8 (3H, t, J=6 Hz), 7.5 (2H, disappears with D₂O), 7.0–7.5 (7H, m), 5.35 (1H, dd), 2.9 (4H, s), 2.7 (5H, s).

EXAMPLE 26

N-(3-(4-Methylphenyl)propyl)-2-hydroxy-2-phenylethanamine

The title compound was prepared in the manner described in Example 9 using phenylglyoxal and 3-(4-Methylphenyl)propanamine. Recrystallization of the chromatographed material from benzene-hexane gave the title compound m.p. 114–116. τ(CDCL₃) 8.15 (2H, m), 7.7 (3H, s), 6.9–7.5 (6H, m+2H, disappears with D₂O), 5.3 (1H, m), 2.9 (4H, s), 2.7 (5H, m).

EXAMPLE 27

N-(3-(4-Methylphenyl)-1-methylpropyl)-2-hydroxy-2-phenyl ethanamine

The title compound was prepared in the manner described in Example 3 using 2-hydroxy-2-phenylethanamine and 3-(4-methylphenyl)butan-2-one. The chromatographed material was recrystallized from hexane to give the title compound m.p. 96–102 as a 19:81 mixture of diastereoisomers. τ(CDCl₃) 8.9 (3H, d, J=6 Hz), 8.1–8.5 (2H, m), 7.7 (3H, s), 7.0–7.6 (5H, m), 7.0 (2H, disappears with D₂O), 5.35 (1H, m), 2.9 (4H, s), 2.6 (5H, m).

EXAMPLE 28

N-(2-(4-Methylphenyl)-1,1-dimethylethyl)-2-hydroxy-2-(3-chlorophenyl)ethanamine

The title compound was prepared in the manner described in Example 9 using 3-chlorophenylglyoxal and 2-(4-Methylphenyl)-1,1-dimethyl ethanamine. The chromatographed material was recrystallized from cyclohexane to give the title compound m.p. 104–105. τ(CDCL₃), 8.9 (6H, s), 7.7 (3H, s), 7.4 (2H, s), 7.1 (2H, dd,), 5.45 (1H, dd), 3.0 (4H, s), 2.5–2.8 (4H, m).

EXAMPLE 29

N-(2-(4-Methylphenyl)-1,1-dimethylethyl)-2-hydroxy-2-phenyl ethanamine

The title compound was prepared in the manner described in Example 9 using phenylglyoxal and 2-(4-methylphenyl)-1,1-dimethylethanamine. The chromatographed material was recrystallized from cyclohexane to give the title compound m.p. 137. τ(CDCl₃+d₆DMSO) 8.95 (6H, s), 7.7 (3H, s), 7.35 (2H, s), 7.0–7.3 (2H, dd), 5.3 (1H, dd), 2.9 (4H, s), 2.5–2.7 (5H, m).

EXAMPLE 30

N-(3-(4-Methylphenyl)-1,1-dimethylpropyl)-2-hydroxy-2-(3-chlorophenyl)ethanamine The title compound was prepared in the manner described in Example 9 using 3-chlorophenylglyoxal and 3-(4-methylphenyl)-1,1-dimethylpropanamine. The chromatographed material was recrystallized from cyclohexane to give the title compound m.p. 136. τ(CDCL₃+d₆DMSO) 8.9 (6H, s), 8.2–8.4 (2H, m), 7.7 (3H, s), 7.0–7.6 (4H, m), 5.35 (1H, dd), 2.9 (4H, s), 2.5–2.7 (5H, m).

EXAMPLE 31

N-(2-(4-Methylphenoxy)-1-methylethyl)-2-hydroxy-2-phenylethanamine

The title compound was prepared in the manner described in Example 3 using 2-hydroxy-2-phenylethanamine and (4-methylphenoxy)propan-2-one. Recrystallization from heptane gave the title compound m.p. 87–105. τ(CDCL₃) 8.9 (3H, d, J=6 Hz), 7.7 (3H, s), 6.7–7.5 (3H, +2H (disappears with D₂O)), 6.2 (2H, m), 5.3 (1H, m), 3.3 (2H, d, J=9 Hz), 2.9 (2H, d, J=9 Hz), 2.7 (5H, m).

EXAMPLE 32

N-(2-(2,4-Dimethylphenyl)-1-methylethyl)-2-hydroxy-2-phenyl ethanamine (6:94)

The title compound was prepared in the manner described in Example 9 using phenylglyoxal and 2-(2,4-dimethylphenyl)-1-methylethanamine. The residual oil was chromatographed on Kieselgel 60 using 3% methanol-chloroform. Recrystallization of the resulting solid from hexane gave the title compound m.p. 91–92 as a 6:94 mixture of diastereoisomers. τ(CDCl₃) 8.9 (3H, d, J=6 Hz), 7.7 (6H, s), 6.9–7.6 (5H, (m) +2H, disappears with D₂O) 5.35 (1H, m), 3.05 (3H, s), 2.68 (5H, m).

EXAMPLE 33

N-(2-(2,4-Dimethylphenyl)-1-methylethyl)-2-hydroxy-2-(3-trifluoromethylphenyl)ethanamine The title compound was prepared in the manner described in Example 9 using 3-trifluoromethylphenylglyoxal and 2-(2,4-dimethylphenyl)-1-methylethanamine. The residual oil was chromatographed on Kieselgel 60, using 3% methanolchloroform as eluent. Treatment of the chromatographed material with ethereal hydrogen chloride gave the hydrochloride salt m.p. 100–110, recrystallised from benzene as a 34:66 mixture of diastereoisomers. τ(CDCl₃) 8.6 (3H, d, J=6 Hz), 7.7 (6H, s), 6.2–7.4 (5H, m+2H (disappears with D₂O)), 4.45 (1H, m), 3.0 (3H, s), 2.2–2.7 (4H, m), 1.2 (1H broad disappears with D₂O), −0.2 (1H, broad, disappears with D₂O).

EXAMPLE 34

N-(2-(2,4-Dimethylphenyl)-1-methylethyl)-2-hydroxy-2-phenyl ethanamine (49:51)

The title compound was reprepared as a 49:51 mixture of diastereoisomers m.p. 58–63 in the manner described in Example 3 using 2-hydroxy-2-phenylethanamine and (2,4-dimethylphenyl)propanone. ¹Hnmr identical with that of Example 32.

EXAMPLE 35

N-(2-(4-Methylphenoxy)-1-methylethyl)-2-hydroxy-2-(3-trifluoromethylphenyl)ethanamine The title compound was prepared in the manner described in Example 3 using 2-hydroxy-2-(3-trifluoromethylphenyl)ethanamine and (4-methylphenoxy)propan-2-one. The residual oil was chromatographed on Kieselgel 60. Elution with 5% methanol-chloroform gave the title compound m.p. 86–96 (heptane). $\tau$(CDCl$_3$) 8.9 (3H, d, J=6 Hz), 7.7 (3H, s), 6.7–7.6 (5H, m, 2H disappears with D$_2$O) 6.0–6.5 (2H, m), 5.3 (1H, m), 3.25 (2H, d, J=9 Hz), 2.95 (2H, d, J=9 Hz), 2.3–2.65 (4H, m).

EXAMPLE 36

N-(2-(4-Methylphenyl)-1-methylethyl)-2-hydroxy-2-(3-ethylphenyl)ethanamine

The title compound was prepared as described in Example 3 using 2-hydroxy-2-(3-ethylphenyl)ethanamine and (4-methylphenyl)propanone. The residual oil was chromatographed on Kieselgel 60. Elution with 2% methanolchloroform gave the title compound, isolated as the hydrochloride salt, as a 54:46 mixture of diastereoisomers m.p. 97–104. $\tau$(d$_6$DMSO) 8.85 (3H, d, J=6 Hz), 8.8 (3H, d, J=6 Hz), 7.7 (3H, s), 7.4 (2H, q, =6 Hz), 6.3–7.2 (5H, m), 4.9 (1H, m), 3.8 (1H, broad, disappears with D$_2$O), 2.8 (4H, s), 2.6–2.8 (4H, m), 1.1+0.2 (2H, broad, both disappear with D$_2$O).

EXAMPLE 37

N-(2-(4-Methylphenyl)-1-methylethyl)-2-hydroxy-2-(4-trifluoromethyl)ethanamine

The title compound was prepared as described in Example 3 using 2-hydroxy-2-(4-trifluoromethylphenyl)ethanamine and (4-methylphenyl)propanone. The residual oil was chromatographed on Kieselgel 60. Elution with 2% methanol-chloroform gave the title compound as a 50:50 mixture of diastereoisomers, mp 85–89 (hexane).

$\tau$ (CDCl$_3$) 8.9 (3H, d, J=6 Hz), 7.7 (3H, s), 6.9–7.7 (7H, m), 5.4 (1H, m), 2.85–3.05 (4H, m), 2.3–2.67 (4H, m).

PREPARATION 1

1-S-2-(4-Methylphenyl)-1-methylethanamine

A mixture of 1-(4-methylphenyl)-propan-2-one (15.3 g) and (−)-α-methylbenzylamine (9.65 g) was stirred in refluxing benzene (150 ml) under a Dean & Stark apparatus until the theoretical amount of water had been collected. The solvent was evaporated and replaced with ethanol (200 ml). Raney Nickel (from 20 ml, of suspension in water, washed several times with ethanol) was added and the mixture was hydrogenated in a Parr hydrogenator at ambient temperature under a hydrogen pressure of 60 psi for 36 h. The catalyst was filtered off and the solvent was evaporated. The residue was taken up in ether (50 ml) and treated with ethereal hydrogen chloride (50 ml). The solid was collected and dried (19.0 g). Recrystallisation from acetonitrile gave N-(1-S-1-phenylethyl)-1-S-2-(4-methylphenyl)-1-methylethanamine as a colourless solid (10.0 g), mp 195°–199°.

$^{13}$C ppm (DMSO d$_6$): 15.93, 19.94, 20.38, 36.78, 52.62, 54.40, 127.83, 128.65, 128.71, 128.93, 133.75, 135.53, 137.41.

The solid prepared above was dissolved in ethanol (200 ml), 5% Pd/C (500 mg) was added and the mixture was shaken in the Parr under a hydrogen pressure of 60 psi at 60° for 8 h. The catalyst was removed, the solvent was evaporated and the residue was recrystallised from ethyl acetate to give 1-S-2-(4-carbomethoxyphenyl)-1-methylethanamine hydrochloride as colourless needles 6.9, mp 200°–202° $[\alpha]_D^{25}$ (water)= +22.5°.

$^1$H $\tau$ (DMSO d$_6$): 8.90 (3h, d, J=6 Hz), 7.76 (3H, s), 7.40 (1H, m), 6.5–7.1 (2H, m), 2.90 (4H, s), 2.6 (3H, br).

PREPARATION 2

1-R-2-(4-Methylphenyl)-1-methylethanamine

N-(1-R-1-phenylethyl)-1-R-2-(4-methylphenyl)-1-methylethanamine hydrochloride was prepared by the method outlined in Preparation 1, replacing 1-(4-carbomethoxyphenyl)propan-2-one with 1-(4-methylphenyl)propan-2-one and (−)-α-methylbenzylamine with (+)-α-methylbenzylamine. Recrystallisation from acetonitrile gave a colourless solid, mp 200°–204°.

$^{13}$C as in Preparation 4.

Debenzylation was achieved as described in Preparation 1 and the title compound (hydrochloride) was obtained as a colourless solid from acetonitrile, mp 202°–203°. $[\alpha]_D^{25}$ (water)= −23.8°.

$^1$H as in Preparation 4.

PREPARATION 3

2-Hydroxy-2-(3-trifluoromethylphenyl)ethanoic acid

A solution of 3-trifluoromethylbenzaldehyde (69.2 g) in ether (250 ml) was shaken with a solution of sodium metabisulphite (84.5 g) in water (85 ml). The mixture was cooled in the refrigerator overnight, the solid was collected, washed with a little propan-2-ol and dried (120 g). The bisulphite addition complex was suspended in a mixture of water (70 ml) and ether (250 ml) with rapid stirring during the addition of a solution of potassium cyanide (28.5 g) in water (85 ml). The mixture was stirred until all the solid was dissolved and the two layers were clear (ca 2 h). The ethereal layer was separated, evaporated and hydrochloric acid (400 ml) was added. The mixture was stirred on the steam bath for 5 h, cooled. The residue was taken up in the minimum amount of 4N sodium hydroxide solution, washed with ether, acidified with hydrochloric acid and extracted into chloroform. The chloroform extracts were dried and evaporated to an oil (61.8 g) which crystallised on standing.

PREPARATION 4

A mixture of rac 2-R-2-hydroxy-2-(3-trifluoromethylphenyl)ethanoic acid (57.4 g) and (+)-ephedrine (43.05 g) in ethanol (100 ml) was warmed until completely dissolved. The solvent was evaporated and the resulting oil was taken up in ether (100 ml) and cooled at −20°. The solid (28 g) was collected and recrystallised from ethanol (18.8 g), mp 101°–110°. A second recrystallisation gave colourless plates (9.7 g), mp 116°–117.5°.

The crystals were treated with 2N hydrochloric acid (50 ml) and the mixture was extracted with chloroform (100 ml) and ether (100 ml). The dried (MgSO$_4$) extracts were evaporated to an oil. $[\alpha]_D^{25}$ (acetone)= −87.9.

PREPARATION 5

2-(R)-2-Hydroxy-2-(3-trifluoromethylphenyl)ethanol

Borane-methylsulphide complex (26.3 ml) was added dropwise to a stirred solution of 2-R-2-hydroxy-2-(3-trifluoromethylphenyl)ethanoic acid (15 g) in dry THF (100 ml) under nitrogen. After the addition of the first few drops of BMS, the mixture was warmed to reflux temperature for the rest of the addition. The mixture was heated under reflux for a further 2 h, then cooled in ice and methanol (25 ml) added dropwise to destroy excess reagent. The solvent was evaporated, the residue taken up in ethyl acetate and dried (MgSO$_4$). Evaporation of the solvent gave the title compound (14 g) which was used without further purification.

τ (CDCl$_3$) 5.5–6.5 (4H, m-2H replaceable by D$_2$O), 4.9 (1H, m), 2.2–2.6 (4H, m).

PREPARATION 6

(R)-3-Trifluoromethylstyrene oxide

A solution of 4-toluene sulphonyl chloride (12.99 g) in toluene (50 ml) was added dropwise to a stirred solution of 2-R-2-hydroxy-2-(3-trifluoromethylphenyl)ethanol (14 g) in pyridine (10 ml) and toluene (50 ml) with ice cooling. The reaction mixture was stood at 0° C. for 48 hours, filtered to remove precipitated pyridinium hydrochloride and the solvent evaporated. The residue was dissolved in chloroform, washed with 2NHCl, water and dried (MgSO$_4$). The solvent was evaporated to give crude 2-R-2-hydroxy-1-(4-toluenesulphonyloxy)-2-(3-trifluoromethylphenyl)ethane (16 g) as an oil. This product was dissolved in dimethyl sulphoxide (30 ml) containing 5N sodium hydroxide (20 ml) and allowed to stand at 0° C. for 16 hours before pouring into ice/water. The product was extracted into 50% hexane/chloroform, dried and evaporated. Distillation of the residue gave the title compound as a clear liquid bp 48°–50°/0.5 mm (4.3 g).

$(\alpha)_D^{25}$ (ethanol) = +2.7°.

τ(CDCl$_3$) 7.3 (1H, m), 6.9 (1H, m), 6.2 (1H, m), 2.4–2.7 (4H, m).

PREPARATION 7

4-Isopropylphenylacetone

A mixture of 4-isopropylbenzaldehyde (29.6 g) and n-butylamine (26 ml) was heated in benzene under reflux in a Dean & Stark apparatus until the theoretical amount of water had been collected. The solvent was evaporated, the residual oil taken up in glacial acetic acid and nitroethane (35 ml) was added. The mixture was stirred and heated for 1h at 95°–105° and on cooling deposited crystals of 1-(4-isopropylphenyl)-2-nitroprop-1-ene (23.8 g).

Concentrated hydrochloric acid (280 ml) was added dropwise over 1h to a suspension of the above nitropropene (23.8 g) and iron powder (40 g) in methanol under reflux. The solution was heated a further 1 h under reflux, cooled, water added and the methanol evaporated. The residue was extracted with ether (×3), the ether layers washed with water (×3) and sodium bicarbonate (×3). The ether layer was dried (MgSO$_4$), evaporated and the residue distilled to give the title compound, bp 92–100/1.5 mm).

τ (CDCl$_3$) 8.75 (6H, d, J=6 Hz), 7.85 (3H, s), 7.1 (1H, h, J=6 Hz), 6.4 (2H, s), 2.8 (4H, s).

PREPARATION 8

4-Ethylphenylacetone 1-(4-Ethylphenyl)-2-nitroprop-1-ene (prepared in the manner described in Preparation 7), (13.6 g) in tetrahydrofuran was added to aluminium amalgam (prepared from aluminium foil (10.7 g) and mercuric chloride (7.3 g) in tetrahydrofuran and the reaction temperature kept to 35°. The reaction mixture was left for 1h at room temperature, filtered, the solvent dried (MgSO$_4$) and evaporated to give 4-ethylphenylacetone oxime (10.2 g) as a brown oil. This was dissolved in methanol and heated under reflux with a solution of sodium metabisulphite (44 g) in water for 6h. Concentrated hydrochloric acid was added to the cooled solution and left at room temperature for 2h. Extraction with chloroform and distillisation gave 4-ethylphenyl acetone, 6.02 g, bp 45/1 mm.

τ (CDCl$_3$) 8.25 (3H, t, J=6 Hz), 8.0 (3H, s), 7.4 (2H, q, J=6 Hz), 6.4 (2H, s), 2.9 (4H, s).

PREPARATION 9

4-t-Butylphenylacetone

Prepared from 4-t-butylbenzaldehyde in the manner described in Preparation 8, bp 94–100/7 mm.

τ (CDCl$_3$) 8.7 (9H, s), 7.9 (3H, s), 6.4 (2H, s), 2.9 (2H, d, J=6 Hz), 2.7 (2H, d, J=6 Hz).

PREPARATION 10

4-(4-Methylphenyl)butan-2-one

3-Carboethoxy-4-(4-methylphenyl)but-2-one (20 g), (prepared by hydrogenation over PtO$_2$ at 1 atmosphere of 3-carboethoxy-4-(4-methylphenyl)but-3-en-2-one) was heated under reflux for 3.5 h in a mixture of glacial acetic acid (48 ml), concentrated hydrochloric acid (5.6 ml) and water (30 ml). The solvent was evaporated, the residue dissolved in xylene, washed with water, dried and evaporated. The residue was distilled to give 4-(4-methylphenyl)butan-2-one, 11.0 g, bp 80–90/1 mm).

PREPARATION 11

2-(4-Methylphenyl)ethanamine

4-Methylbenzyl cyanide (10 g) in ether was added dropwise under nitrogen to lithium aluminium hydride (2.9 g) in ether. The solution was refluxed for 1 h at the end of addition. The reaction mixture was cooled, water (3 ml), 2N.NaOH (3 ml), and further water (9 ml) were added, the reaction mixture filtered, the residue washed with chloroform and the combined solvents dried (MgSO$_4$). Evaporation gave 2-(4-methylphenyl)ethanamine (11.59 g).

PREPARATION 12

3-(4-Methylphenyl)propanamine 2-(4-Methylphenyl)propionamide (4 g) in dry tetrahydrofuran was added dropwise under nitrogen to lithium alumimium hydride (0.93 g) in dry tetrahydrofuran. The mixture was refluxed for 1 h at the end of addition. Water (1 ml), 2N. NaOH (1 ml), further water (3 ml) were added, the mixture filtered and the filtrate evaporated to give 3-(4-methylphenyl)propanamine (3.5 g).

PREPARATION 13

2-(4-Methylphenyl)-1,1-dimethylethanamine and 3-(4-Methylphenyl)-1,1-dimethylpropanamine were prepared in an analogous manner to that described for 2-phenyl-1,1-dimethylethanamine (Org. Syn. Coll. Vol. IV. 471).

DEMONSTRATION OF EFFECTIVENESS OF COMPOUNDS

(i) Anti-obesity Activity

The compounds were administered by oral gavage in water or carboxymethyl-cellulose suspension to genetically obese mice daily for 28 days. At the end of the time the carcass composition was determined. The results obtained were as follows:

| COMPOUND OF EXAMPLE | DOSE mg/kg po | g LIPID/MOUSE: | |
|---|---|---|---|
| | | TREATED | CONTROL |
| 1 mg 106-109 | 4.2 | 19.38 | 21.15 |
| 3 mg 98-103 | 9.1 | 13.99 | 16.87 |
| 4 | 9.0 | 16.40 | 21.30 |
| 5 | 12.6 | 14.48 | 20.10 |
| 6 | 8.8 | 16.68 | 20.83 |
| 7 | 7.5 | 16.22 | 20.10 |
| 9 | 11.5 | 18.04 | 21.34 |
| 11 | 11.0 | 20.22 | 21.92 |
| 12 | 11.0 | 16.97 | 21.92 |
| 15 | 10.0 | 19.31 | 22.03 |
| 19 | 28.4 | 20.74 | 22.03 |
| 20 | 8.4 | 14.72 | 21.10 |
| 32 (18 days) | 7.9 | 19.52 | 21.76 |
| 35 | 9.8 | 21.90 | 24.85 |

(ii) EFFECT ON ENERGY EXPENDITURE

The effect of the compounds on the energy expenditure of mice was demonstrated by means of the following procedure:

Female CFLP mice each weighing approximately 24 g, were given food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 21 hours after dosing from the volume of air leaving the boxes and its oxygen content, following the principles described in J. B. de V. Weir, *J. Physiol.* (London) 109, 1–9 (1949). The food intake of the mice was measured over this same period of 21 hours. The results are expressed as a percentage of the mean food intake or rate of energy expenditure of the mice dosed with water.

| COMPOUND OF EXAMPLE NO. | DOSE mg/kg po | MEAN ENERGY EXPENDITURE | MEAN FOOD INTAKE |
|---|---|---|---|
| | | (0.3 h) (0.21 h) | |
| Control | — | 100 100 | 100 |
| 1 mp 76-78 | 17 | 169 143 | 101 |
| 1 mp 106-9 | 17 | 143 126 | 105 |
| 2 | 23 | 154 106 | 87 |
| 3 mp 74-94 | 15 | 156 115 | 97 |
| 3 mp 98-103 | 15 | 126 99 | 86 |
| 4 | 18 | 175 127 | 87 |
| 5 | 25 | 140 132 | 94 |
| 6 | 18 | 137 111 | 89 |
| 7 | 7.5 | 137 105 | 87 |
| 8 | 17 | 153 121 | 87 |
| 9 | 23 | 115 100 | 93 |
| 10 | 7.5 | 160 129 | 94 |
| 11 | 11 | 122 111 | 91 |
| 12 | 11 | 139 125 | 82 |
| 13 | 19.5 | 148 121 | 79 |
| 14 | 22.5 | 171 126 | 93 |
| 15 | 20 | 138 116 | 77 |
| 16 | 19.5 | 112 100 | 90 |
| 17 | 16.5 | 117 101 | 99 |
| 18 | 26.8 | 96 90 | 92 |
| 19 | 14.2 | 125 103 | 97 |
| 20 | 16.9 | 145 115 | 79 |
| 21 | 19.4 | 123 102 | 94 |
| 22 | 20 | 133 110 | 86 |
| 23 | 18.7 | 122 103 | 93 |

| COMPOUND OF EXAMPLE NO. | DOSE mg/kg po | MEAN ENERGY EXPENDITURE | MEAN FOOD INTAKE |
|---|---|---|---|
| 24 | 16.6 | 154 | 122 | 90 |
| 25 | 16.2 | 150 | 110 | 106 |
| 26 | 14.9 | 127 | 108 | 116 |
| 27 | 15.8 | 125 | 104* (0–12 h) | — |
| 28 | 17.7 | 123 (0–3 h) | 113 (0–21 h) | 82 |
| 29 | 15.7 | 116 | 105 | 94 |
| 30 | 18.4 | 125 | 106 | 88 |
| 31 | 15.9 | 123 | 100 | 103 |
| 32 | 15.7 | 143 | 111 | 122 |
| 33 | 21.5 | 122 | 105 | 92 |
| 34 | 15.7 | 150 | 108 | 89 |
| 35 | 19.6 | 115 | 113 | 118 |
| 36 | 18.5 | 125 | 106 | 95 |

(iii) Cardiac Activity

Rat hearts were perfused by the Langendorff procedure. Hearts were dissected free within 30 seconds of death and reverse perfused via the aorta and coronary vessels with Krebs-Ringer bicarbonate solution (pH 7.4, 37° C.) gassed with 95% oxygen:5% carbon dioxide at a flow rate between 8–12 cm$^3$/minute. Responses were observed after injection of drug dissolved in isotonic saline into the perfusion media. Heart rate and tension were displayed on an Ormed MX2P recorder via a tension transducer and heart ratemeter.

Results are expressed as a percentage of the maximum response due to salbutamol.

| COMPOUND OF EXAMPLE NO. | DOSE ADDED TO PERFUSATE (μg) | HEART TENSION | HEART RATE |
|---|---|---|---|
| Salbutamol | — | 100.0 | 100 |
| 1 mp 76-78 | 30 | 6.5 | 13 |
| 1 mp 106-9 | 30 | 13.0 | 45 |
| 2 | 10 | 17.0 | 20 |
| 3 mp 74-94 | 30 | 19.0 | 10 |
| 3 mp 98-103 | 30 | 19.0 | 0 |
| 4 | 30 | 25.0 | 40 |
| 5 | 10 | 0 | 0 |
| 6 | 30 | 10.0 | 0 |
| 7 | 30 | 10.0 | <0 |
| 8 | 30 | 54.0 | 92 |
| 9 | 30 | 12.5 | 9 |
| 10 | 30 | 33.0 | 29 |
| 11 | 30 | 12.0 | 6.5 |
| 12 | 30 | 7.0 | 1.5 |
| 13 | 30 | 37.0 | 0 |
| 14 | 30 | 21.0 | 25 |
| 15 | 30 | 4.5 | 4 |
| 16 | 30 | 0 | 0 |
| 17 | 30 | 0 | 0 |
| 19 | 30 | 0 | 0 |
| 20 | 30 | <0 | 12 |
| 22 | 30 | 0 | 0 |
| 23 | 30 | <0 | 0 |
| 24 | 30 | 0 | 4 |
| 25 | 30 | 36.0 | 15 |
| 26 | 30 | 44.0 | 0 |
| 27 | 30 | 18.0 | 0 |
| 28 | 30 | 89.0 | 67 |
| 29 | 30 | 0 | 0 |
| 30 | 30 | 11.0 | 0 |
| 33 | 30 | 6.0 | 0 |
| 34 | 30 | 50.0 | 3.5 |
| 35 | 30 | 0 | 0 |

(iv) Hypoglycaemic Activity

Female CFLP mice, weighing approximately 25 g, were fasted for 24 h prior to the study. The compounds under study were administered orally as an aqueous solution to each of 8 mice. 30 minutes later a blood sample (20 cm³) was obtained from the tail for the analysis of blood glucose. Immediately after taking this blood sample, glucose (1 g/kg body weight) was administered subcutaneously to each mouse. 8 mice were given water as a control. Blood samples were then obtained from each mouse at 30 minute intervals for 120 minutes.

Compounds that produced a significant ($P<0.05$) reduction of blood glucose, compared with control mice given water, at any time interval, were considered active. The area under the blood glucose curve over the 2 h period after the administration of the glucose was calculated for each compound and compared with the value for control animals.

| COMPOUND OF EXAMPLE NO. | DOSE mg/kg | % REDUCTION IN AREA UNDER BLOOD GLUCOSE CURVE |
|---|---|---|
| 1 mp 76–78 | 1.0 | 44.0 |
| 4 | 1.0 | 35.0 |
| 5 | 1.0 | 29.0 |
| 10 | 1.0 | 48.0 |
| 12 | 0.56 | 37.2 |
| 15 | 4.5 | 53.0 |
| 18 | 60.0 | 22.6 |
| 23 | 4.0 | 46.0 |
| 33 | 4.8 | 17.0 |
| 35 | 17.65 | 25.0 |

(v) Anti-Inflammatory Activity

The method used is based on that described by G. Tonelli et al (Endocrinology, 77, 625–634, 1965). An inflammation is induced in the rat ear by the application of 50 μl of a 1% solution of croton oil in tetrahydrofuran, test compounds being dissolved in the irritant vehicle. After 6 hours the inflammation is assessed by killing the animals and weighing the ears. Topical anti-inflammatory activity of a compound is generally considered to be shown when a significant (5% level) reduction in ear weight is seen compared to non-drug treated control.

| COMPOUND OF EXAMPLE NO. | DOSE mg/rat ear | ACTIVITY |
|---|---|---|
| 5 | 2.2 | Active |
| 37 | 2.5 | Active |

Toxicity

No toxic effects were observed in any of the above tests.

I claim:

1. A compound of formula (II):

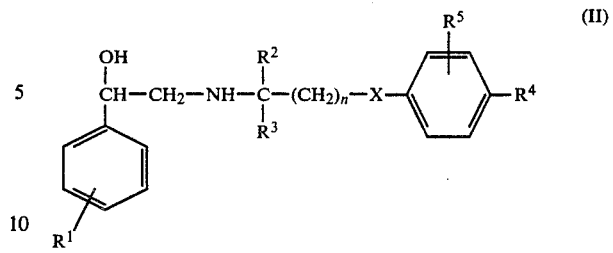

or a pharmaceutically acceptable salt thereof, in which X is a bond, $R^1$ is in the meta position in the phenyl ring and is a hydrogen, fluorine, chlorine or bromine atom or a trifluoromethyl or $C_{1-4}$ alkyl group, each of $R^2$ and $R^3$ is a hydrogen atom or a $C_{1-4}$ alkyl group, $R^4$ is a $C_{1-4}$ alkyl group, $R^5$ is a hydrogen atom or a $C_{1-4}$ alkyl group and n is an integer of from 1 to 3.

2. A compound of formula (III):

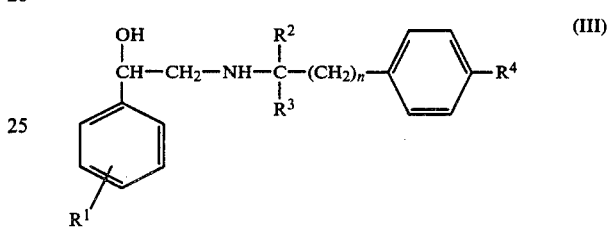

in which $R^1$ is in the meta position in the phenyl ring and is a hydrogen, fluorine, chlorine or bromine atom or a trifluoromethyl group, each of $R^2$ and $R^3$ is a hydrogen atom or a $C_1$ to $C_4$ alkyl group, $R^4$ is a $C_1$ to $C_4$ alkyl group and n is an integer of from 1 to 3.

3. A compound according to claim 1, in which each of $R^2$ and $R^3$ is a hydrogen atom or a methyl group.

4. A compound according to claim 1, in which n is 1.

5. A compound according to claim 1, in which $R^4$ is a methyl group.

6. A pharmaceutical composition having anti-obesity and hypoglycaemic activity comprising an anti-obesity and hypoglycaemic amount of a compound to formula (II) as defined in claim 1 together with a pharmaceutically acceptable carrier.

7. A pharmaceutical composition according to claim 6, in unit dosage form.

8. A composition according to claim 7, in which each unit dose contains from 0.01 to 500 mg of a compound of formula (II).

9. A method of treating obesity in human or non-human animals, which comprises administering an effective, non-toxic amount of a compound of formula (II), as defined in claim 1 or a pharmaceutically acceptable salt thereof, to the obese animals.

10. A method of treating hyperglycaemia in humans, which comprises administering a hypoglycaemically effective, non-toxic amount of a compound of formula (II), as defined in claim 1 or a pharmaceutically acceptable salt thereof to hyperglycaemic humans.

11. A method of treating inflammation in human or non-human animals, which comprises administering an anti-inflammatory non-toxic effective amount of a compound of formula (II), as defined in claim 1 or a pharmaceutically acceptable salt thereof, to the animals.

12. A pharmaceutical composition having anti-obesity and hypoglycaemic activity comprising an anti-obesity and hypoglycaemic amount of a compound of formula (III) as defined in claim 2 together with a pharmaceutically acceptable carrier.

* * * * *